(12) United States Patent
Shippert

(10) Patent No.: US 7,794,449 B2
(45) Date of Patent: Sep. 14, 2010

(54) TISSUE TRANSPLANTATION METHOD AND APPARATUS

(76) Inventor: Ronald D. Shippert, 4975 S. Albion St., Littleton, CO (US) 80121

( * ) Notice: Subject to any disclaimer, the term of this patent is extended or adjusted under 35 U.S.C. 154(b) by 1382 days.

(21) Appl. No.: 11/088,598

(22) Filed: Mar. 23, 2005

(65) Prior Publication Data

US 2006/0213374 A1 Sep. 28, 2006

(51) Int. Cl.
*A61M 1/00* (2006.01)
(52) U.S. Cl. .......................... 604/542; 604/36; 604/37; 604/38; 604/121; 604/191; 604/218; 604/236; 604/237; 604/541
(58) Field of Classification Search .............. 604/237, 604/542, 541
See application file for complete search history.

(56) References Cited

U.S. PATENT DOCUMENTS

| | | | |
|---|---|---|---|
| 1,138,764 A * | 5/1915 | Kline | .......................... 215/358 |
| 4,359,049 A | 11/1982 | Redl et al. | |
| 4,548,207 A | 10/1985 | Reimels | |
| 4,683,884 A | 8/1987 | Hatfield et al. | |
| 4,753,634 A | 6/1988 | Johnson | |
| 4,770,187 A | 9/1988 | Lash et al. | |
| D298,650 S | 11/1988 | Lash | |
| 4,834,703 A | 5/1989 | Dubrul et al. | |
| 4,883,755 A | 11/1989 | Carabasi et al. | |
| 4,957,492 A | 9/1990 | McVay | |
| 5,035,708 A | 7/1991 | Alchas et al. | |
| 5,049,146 A | 9/1991 | Bringham et al. | |
| 5,052,999 A | 10/1991 | Klein | |
| 5,312,380 A | 5/1994 | Alchas et al. | |
| 5,338,294 A | 8/1994 | Blake, III | |
| 5,352,194 A | 10/1994 | Greco et al. | |

(Continued)

FOREIGN PATENT DOCUMENTS

EP 1531881 5/2005

(Continued)

OTHER PUBLICATIONS

Genesis Biosystems, Advancing the Science of Skincare, LipiVage, 3 pages, at http://www.dermagenesis.com/prodlipivage.cfm, printed Mar. 16, 2005.

(Continued)

*Primary Examiner*—Tatyana Zalukaeva
*Assistant Examiner*—Ilya Y Treyger
(74) *Attorney, Agent, or Firm*—Sheridan Ross P.C.

(57) ABSTRACT

The present invention provides for the transplantation of tissue from a donor site in a body to a recipient site. The device includes an outer chamber having an interior volume in which a perforated inner chamber can be placed. During the aspiration of tissue, a vacuum is formed in the interior volume of the outer chamber, to draw tissue from a cannula into the perforated inner chamber. The perforations are sized such that fat is collected within the inner chamber, while fluids and other materials are drawn through the perforations, away from the collected fat. For reinjection, the inner chamber can be removed from the outer chamber, and a sleeve positioned to cover the perforations and thereby form a syringe body that can be interconnected to a needle and plunger for reinjection of the collected fat.

26 Claims, 10 Drawing Sheets

U.S. PATENT DOCUMENTS

| | | | |
|---|---|---|---|
| 5,352,410 | A | 10/1994 | Hansen et al. |
| 5,372,945 | A | 12/1994 | Alchas et al. |
| 5,441,539 | A | 8/1995 | Alchas et al. |
| 5,569,178 | A | 10/1996 | Henley |
| 5,603,845 | A | 2/1997 | Holm |
| 5,766,134 | A | 6/1998 | Lisak et al. |
| 5,786,207 | A | 7/1998 | Katz et al. |
| 5,804,366 | A | 9/1998 | Hu et al. |
| 5,827,217 | A | 10/1998 | Silver et al. |
| 5,911,700 | A | 6/1999 | Mozsary et al. |
| 5,976,470 | A | 11/1999 | Maiefski et al. |
| 6,013,048 | A | 1/2000 | Podany et al. |
| 6,024,725 | A | 2/2000 | Bollinger et al. |
| 6,258,054 | B1 | 7/2001 | Mozsary et al. |
| 6,299,763 | B1 | 10/2001 | Ashman |
| 6,303,286 | B1 | 10/2001 | Dennis et al. |
| 6,315,756 | B1 | 11/2001 | Tankovich |
| 6,316,247 | B1 | 11/2001 | Katz et al. |
| 6,468,225 | B1 | 10/2002 | Lundgren |
| 6,494,876 | B1 | 12/2002 | Fowler et al. |
| 6,623,733 | B1 | 9/2003 | Hossainy et al. |
| 6,626,890 | B2 | 9/2003 | Nguyen et al. |
| 6,777,234 | B1 | 8/2004 | Dennis et al. |
| 7,097,690 | B2 | 8/2006 | Usher et al. |
| 7,335,513 | B2 | 2/2008 | Smith |
| 7,687,059 | B2 | 3/2010 | Fraser et al. |
| 2002/0146817 | A1 | 10/2002 | Cannon et al. |
| 2002/0198474 | A1 | 12/2002 | Becker |
| 2003/0161816 | A1 | 8/2003 | Fraser et al. |
| 2003/0162707 | A1 | 8/2003 | Fraser et al. |
| 2004/0067219 | A1 | 4/2004 | Vida |
| 2004/0097867 | A1 | 5/2004 | Fraser et al. |
| 2004/0106196 | A1 | 6/2004 | Fraser et al. |
| 2005/0025755 | A1 | 2/2005 | Hedrick et al. |
| 2005/0084961 | A1 | 4/2005 | Hedrick et al. |
| 2005/0186671 | A1 | 8/2005 | Cannon et al. |
| 2006/0093527 | A1 | 5/2006 | Buss |
| 2006/0258004 | A1 | 11/2006 | Kosnik et al. |
| 2008/0014181 | A1 | 1/2008 | Ariff et al. |
| 2008/0058763 | A1 | 3/2008 | Boland et al. |
| 2009/0192454 | A1 | 7/2009 | Boland et al. |

FOREIGN PATENT DOCUMENTS

| | | | |
|---|---|---|---|
| EP | 1531882 | | 5/2005 |
| EP | 1921133 | A2 | 5/2008 |
| WO | WO 00/77164 | A1 | 12/2000 |
| WO | WO 2004/067065 | | 8/2004 |
| WO | WO-2004/067065 | A1 | 8/2004 |
| WO | WO-2005/011569 | | 2/2005 |
| WO | WO 2005/011569 | A2 | 2/2005 |
| WO | WO 2005/012480 | A2 | 2/2005 |
| WO | WO 2005/034843 | A2 | 4/2005 |
| WO | WO 2005/095581 | A1 | 10/2005 |
| WO | WO 2006/014156 | A1 | 2/2006 |
| WO | WO 2006/014159 | A2 | 2/2006 |
| WO | WO 2006/022612 | A2 | 3/2006 |
| WO | WO 2006/026969 | | 3/2006 |
| WO | WO 2006/127007 | A2 | 11/2006 |
| WO | WO 2009/149691 | | 12/2009 |

OTHER PUBLICATIONS

LipiVage, product insert, 2 pages, Aug. 2004.

Genesis Biosystems, Advancing the Science of Skincare, LipiVage, 1 page, at http://www.dermagenesis.com/prodlipivage.cfm, printed Oct. 25, 2004.

Office Action for U.S. Appl. No. 11/742,452, filed Apr. 30, 2007, mailed May 12, 2009, pp. 1-7.

Restriction Requirement for U.S. Appl. No. 11/553,920, filed Oct. 27, 2006, mailed Feb. 12, 2009, pp. 1-5.

Restriction Requirement for U.S. Appl. No. 11/742,452, filed Apr. 30, 2007, mailed Feb. 20, 2009, pp. 1-5.

Lee W. Young, International Search Report for International (PCT) Patent Application No. PCT/US 08/59469, mailed Aug. 28, 2008, pp. 1-3.

Lee W. Young, Written Opinion for International (PCT) Patent Application No. PCT/US 08/59469, mailed Aug. 28, 2008, pp. 1-5.

LipiVage Fat Harvest, Wash & Transfer System, available at www.lipivage.com, Genesis Biosystems, Inc., 2 pages, printed Sep. 21, 2005.

Office Action for U.S. Appl. No. 11/553,921, mailed Jul. 7, 2009, pp. 1-11.

Notice of Allowance for U.S. Appl. No. 11/742,452, mailed Jan. 4, 2010, 4 pages.

Final Office Action for U.S. Appl. No. 11/742,452, mailed Nov. 6, 2009, 10 pages.

Interview Summary for U.S. Appl. No. 11/742,452, mailed Dec. 16, 2009, pp. 1-3.

Final Office Action for U.S. Appl. No. 11/553,920, mailed Mar. 26, 2010, pp. 1-11.

U.S. Appl. No. 12/434,073, filed May 1, 2009, patent application and figures as filed.

U.S. Appl. No. 12/484,781, filed Jun. 15, 2009, patent application and figures as filed.

Interview Summary for U.S. Appl. No. 11/553,920, mailed May 19, 2010, 4 pages.

Notice of Allowance and Fee(s) Due for U.S. Appl. No. 11/553,920, mailed Jun. 10, 2010, 8 pages.

\* cited by examiner

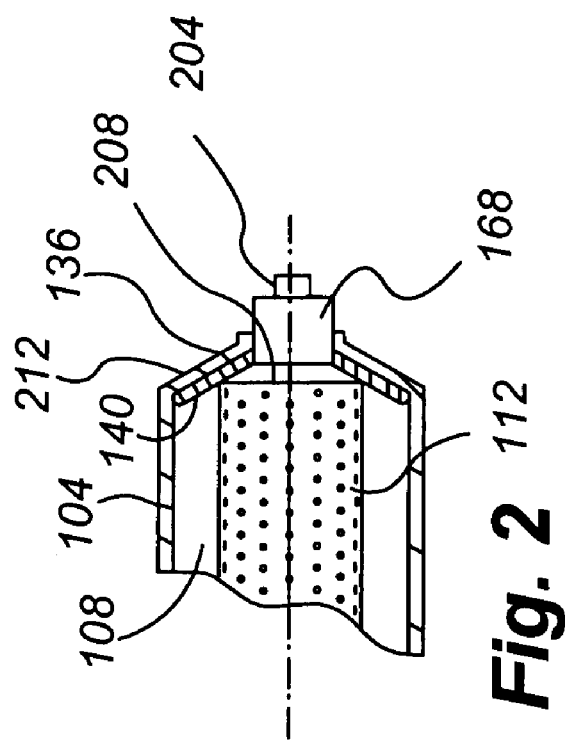
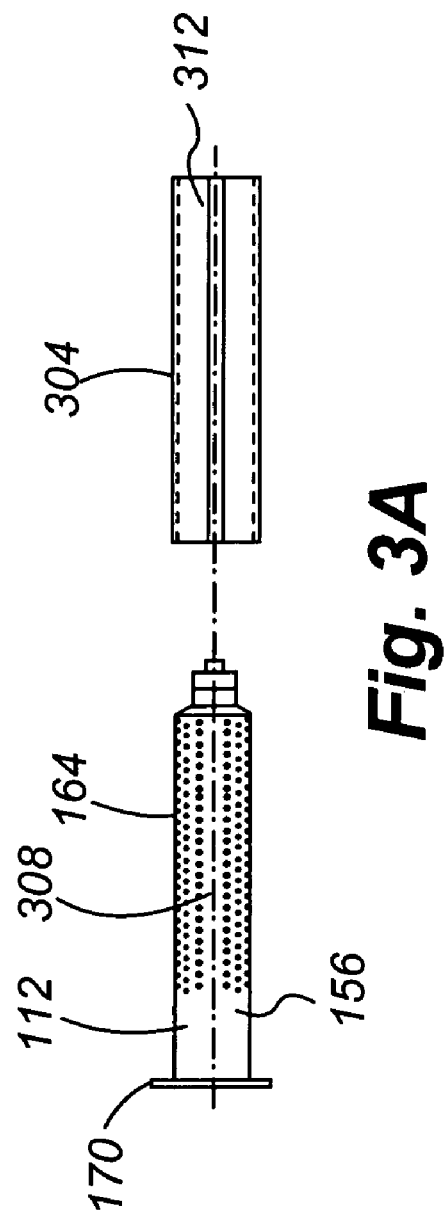

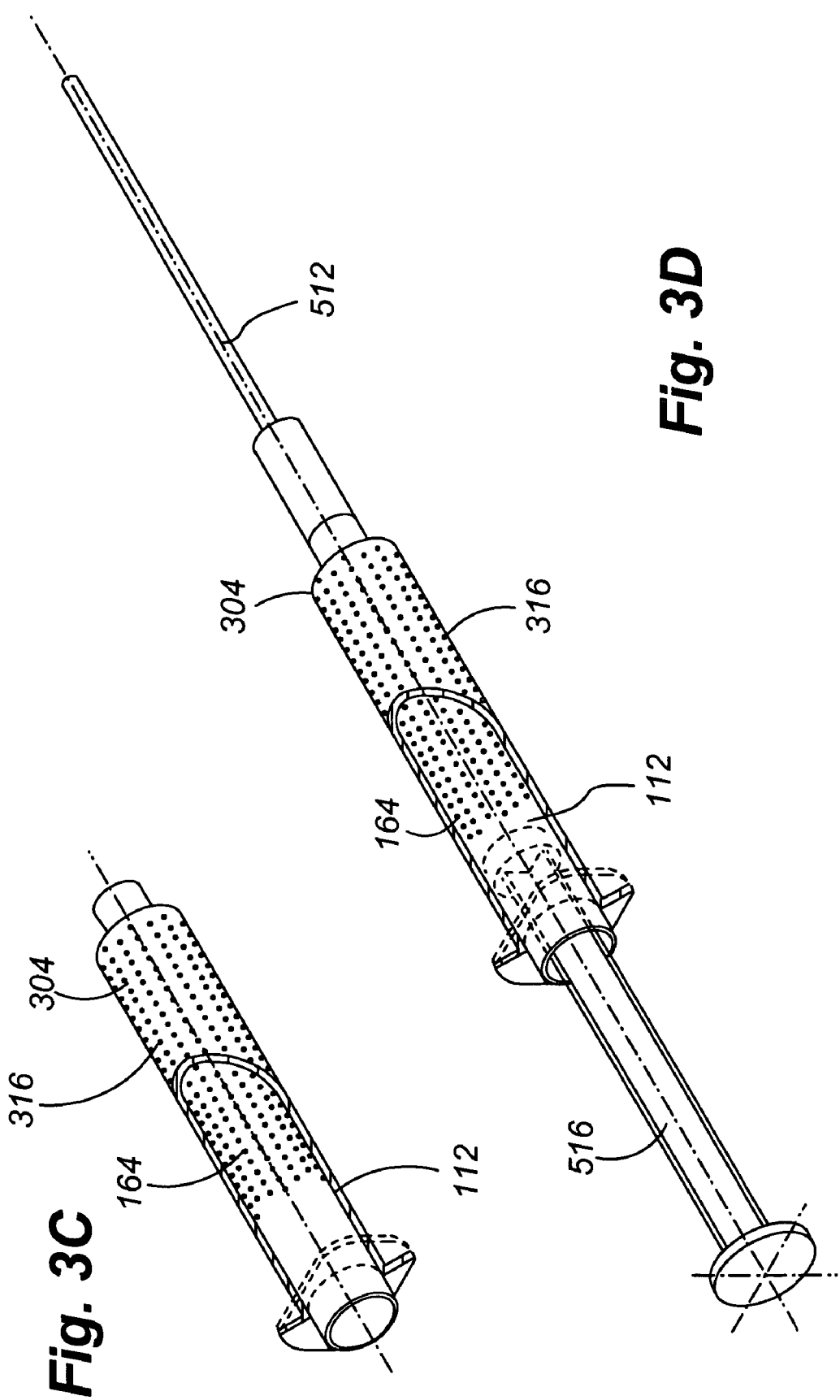

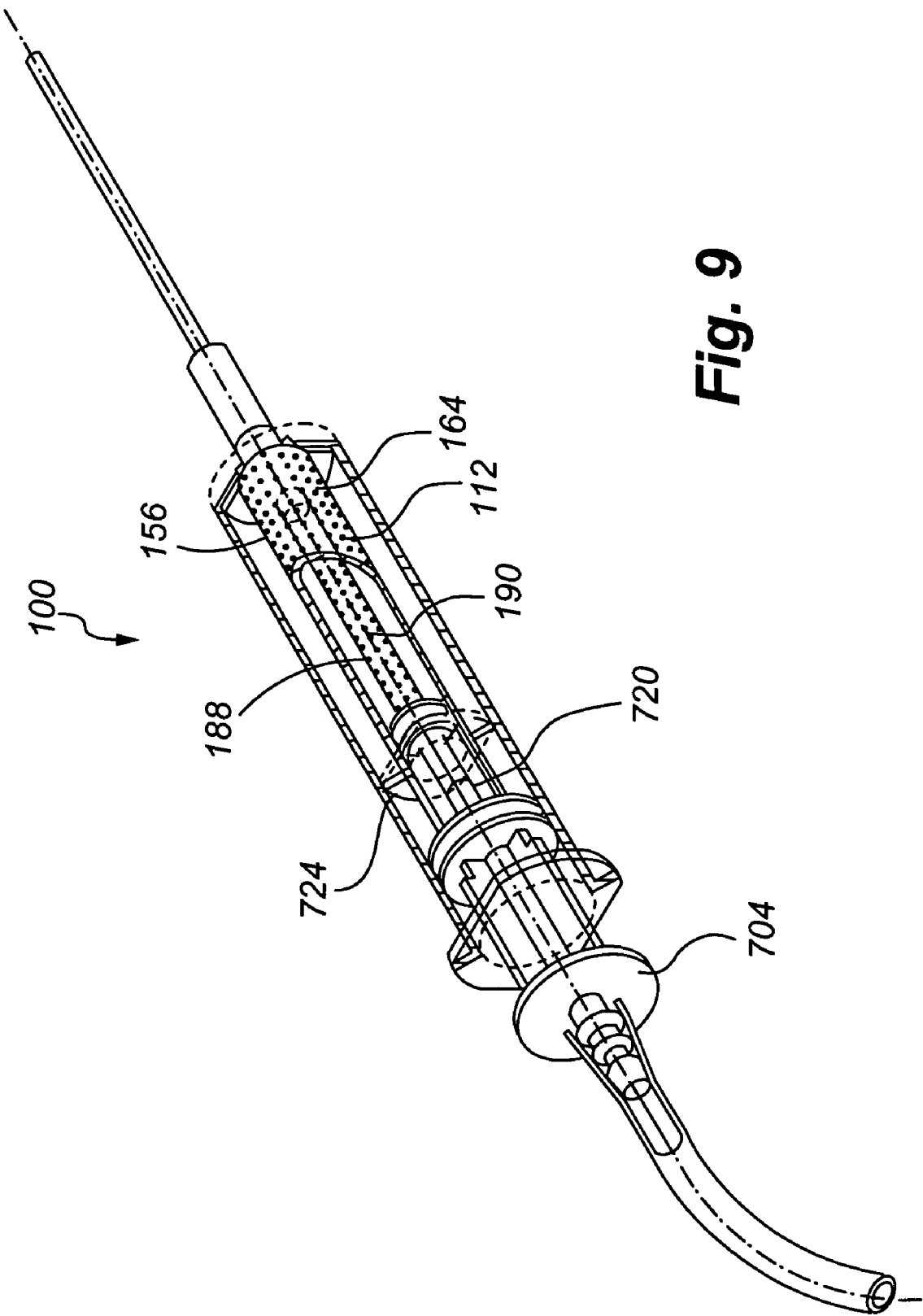

TISSUE TRANSPLANTATION METHOD AND APPARATUS

FIELD OF THE INVENTION

The present invention is directed to the transplantation of tissue in bodies.

BACKGROUND OF THE INVENTION

Microlipoinjection is a process in which fat is taken by a cannula from one spot in the body and reinjected in another place in the body. Microlipoinjection has also been known as liposuction with fat transfer or fat transplantation. In general, microlipoinjection is performed to treat divots and scar indentations from trauma to the face or body, such as may occur as a secondary effect of domestic trauma, surgery or infection. Microlipoinjection can also be used to treat the effects of the loss of the subcutaneous layer of fat due to the normal aging process, either alone or in combination with facelift and fat grafting techniques. Microlipoinjection can also be used for providing filler to reapproximate weakened vocal chords, fill sinuses, or partially close incompetent valves.

Up to about 1990, there were few artificial filler substances available to surgeons. Accordingly, surgeons used human bone, collagen and fat as fillers. However, the use of fat was not very successful, because the instruments and techniques were not sufficiently refined. For example, 50% of the fat may not have lived through the transplantation process. As a result, surgeons would need to implant more fat than would be required if all of the fat survived the process, or the transplantation process would have to be repeated multiple times.

More recently, a number of filler substances, such as Restylane Hyaluronic Acid, Collagen, Fibril, ePTFE (Teflon®), Hylan B Gel, Artecol, BioBlastique and have been used. These substances have proved effective at filling small areas, but the cost for larger areas has become prohibitive. For this reason, as well as interest in the "natural substance" concept, surgeons and their patients have again looked at using fat as a filler.

With the renewed interest in using fat as a filler, techniques have been refined to provide a better fat graft "take" with revascularization. However, the instruments and devices conventionally available to perform the procedure remain clumsy and ill-suited for the procedure. As a result, the procedure has remained difficult to perform, cumbersome, time consuming, expensive and relatively unsuccessful. For example, the conventional process employed in connection with microlipoinjection comprises about 10 steps, some of which can cause damage to a significant percentage of the fat cells. In addition, it is necessary to maintain strict sterility throughout all of the steps. However, sterility is difficult to maintain in connection with centrifuging, which is performed separately from the sterile operating field, and involves ancillary personnel. The basic steps of the conventional microlipoinjection process can be summarized as follows:

Step 1—Liposuction of fat from the donor area, the fat going into a large syringe. The suction aspirate contains the wanted fat, plus the unwanted blood, serum, anesthetic agent, etc. These later substances must be removed for the best lipocyte survival rates.

Step 2—Fat is transferred into several smaller syringes that will fit into a centrifuge. Every time the fat is transferred to another syringe, there is more destruction of fat cells secondary to pressure of the plunger forcing the fat through the narrow outlet of the syringe into the input luer of the next syringe. Caps are placed on the end of the syringe to prevent loss during centrifuging.

Step 3—Centrifuge for several minutes or until the contents are in three layers: the top layer is triglyceride oils, the middle layer is fat, and the lower layer is the remaining blood cell debris.

Step 4—Decant off the top liquid oil and serum from the centrifuge specimen.

Step 5—Place the plunger in the syringe, tip syringe upward and squirt out the red cells and debris, leaving the residual fat in the syringe. Sometimes this has to be repeated, including repeat centrifuging, a number of times for proper separation.

Step 6—Treat contents with irrigation solutions, platelet rich plasma (PRP), albumin, growth hormone, or other substances, by aspirating this substance into the syringe. These substances are considered helpful in ensuring the viability of the lipocyte (fat cell). Some of these substances aid in angiogenesis (establishment of blood vessels) or treat in a manner that encourages lipocyte survival.

Step 7—Gently mix by circular motion.

Step 8—Centrifuge again.

Step 9—Decant off liquid additive.

Step 10—Put the plunger back into the syringe, place an injection needle on the tip and inject the fat into the divot or wrinkle. This injection is conventionally done manually with a control syringe or special manual mechanical gun.

SUMMARY OF THE INVENTION

In accordance with embodiments of the present invention, tissue transplantation methods and apparatuses are provided in connection with the removal of tissue from a donor site, the processing of that tissue, and the reinjection of that tissue into a recipient site. Furthermore, embodiments of the present invention eliminate or minimize the need for centrifuging of removed fats and other processing steps that have been part of the conventional tissue transplantation process. More particularly, a perforated chamber is provided to collect fat and filter unwanted substances from that fat. In addition, the same perforated chamber used to collect removed fat provides a reservoir from which fat can be injected into the body. Accordingly, embodiments of the present invention eliminate the need to transfer fat between a number of different vessels in order to process that fat and prepare it for injection, allowing harvest, separation, treatment and reinjection through the same syringe body.

In accordance with embodiments of the present invention, an apparatus comprising a substantially rigid outer chamber defining an interior volume in which a perforated inner chamber may be placed is provided. The substantially rigid outer chamber includes an outlet fitting through which the interior volume may be placed in communication with a vacuum source, and an inlet fitting through which the inner chamber can be interconnected to a cannula, either directly or through an intermediate conduit. The inner chamber includes a plurality of perforations sized so as to allow fat tissue drawn into the inner chamber by a vacuum created in the interior of the outer chamber to be collected within the inner chamber, while blood, serum and other materials are drawn out of the inner chamber, away from the collected fat.

In accordance with embodiments of the present invention, the outer chamber is provided with an end plug, allowing the inner chamber to be removed from the outer chamber when the end plug is removed. The end plug may additionally incorporate the outlet fitting for interconnecting the interior volume of the outer chamber to a vacuum source. The inner chamber may also include a removable end plug. In general, the end plug is in place while the device is being used to collect fat removed from a body. In accordance with still other embodiments of the present invention, end plugs for the outer and inner chambers are provided as a single integrated plug unit.

For reinjection of the fat, the inner chamber is removed from the outer chamber, and a sleeve is provided to cover the inner chamber perforations. The inner chamber end plug or integrated plug unit is removed from the inner chamber, and a plunger is inserted into the open proximal end of the inner chamber. In addition, the cannula used for tissue aspiration may be disconnected from the inner chamber, and replaced by a reinjection cannula or needle. Accordingly, the inner chamber may function as part of a conventional syringe.

In accordance with still other embodiments of the present invention, the end plug of the perforated inner chamber (or the integrated plug unit for embodiments including an integrated plug unit) may incorporate an inner suction tube having a number of perforations. The inner suction tube may be used to increase the effective filtering surface of the inner chamber and allow fluids and other matter to be drawn from collected fat from the center of the perforated chamber. In accordance with further embodiments, the end plug of the perforated inner chamber (or the integrated plug unit for embodiments including an integrated plug unit) may be fitted with an absorbent material to assist in the separation of such material from collected fat.

In accordance with other embodiments of the present invention, the outer chamber may be sized so that a number of perforated inner chambers may be housed therein. According to such embodiments, a manifold may be used to interconnect the inlets of each of the perforated inner chambers in use to a tissue aspiration cannula through an intermediate conduit. The inner chambers of such embodiments may be similar or identical to inner chambers used in connection with an outer chamber capable of housing only one inner chamber.

In accordance with still other embodiments of the present invention, a fluid reservoir may be provided for instilling an additive or other fluid into collected tissue. The fluid reservoir may be selectively placed in communication with a conduit transferring tissue from a cannula to the inner chamber through a valve. The fluid reservoir may additionally comprise a syringe.

In accordance with embodiments of the present invention, a method for tissue transplantation is provided according to which tissue removed from a donor site using a cannula is collected in a perforated chamber. The same vacuum used to collect the tissue in the perforated chamber draws unwanted liquids and other matter away from the collected fat. The perforated inner chamber can then be removed from the outer chamber, the perforations can be blocked using a sleeve, and a plug in the proximal end of the perforated inner chamber can be removed. By interconnecting a needle to the distal end of the perforated inner chamber, and by inserting a plunger into the proximal end of the perforated inner chamber, fat can be reinjected directly from the perforated inner chamber. Accordingly, no intermediate steps that involve removing the fat from the perforated inner chamber are required for processing or to otherwise prepare the fat for reinjection.

In accordance with still other embodiments of the present invention, an additive or other fluid may be instilled in the aspirated tissue. The additive or other fluid may be introduced at the same time tissue is being deposited in the perforated inner chamber. This can be done by manual injection of the liquids or by opening a connecting valve and utilizing the same suction that is used to extract the tissue through the Bernoulli effect. Alternatively or in addition, fluid may be used to wash and/or treat the collected tissue after that tissue has been deposited in the perforated inner chamber.

BRIEF DESCRIPTION OF THE DRAWINGS

FIG. 2 is a partial cross-section of components of a device for tissue transplantation in accordance with embodiments of the present invention;

FIGS. 3A-3B are views of a perforated chamber and sleeve in accordance with embodiments of the present invention;

FIGS. 3C-3D are views of a perforated chamber and perforated sleeve in accordance with other embodiments of the present invention;

FIG. 9 is a partially cutaway perspective view of a device for tissue transplantation in accordance with other embodiments of the present invention.

DETAILED DESCRIPTION

Embodiments of the present invention generally enable or facilitate tissue transplantation in accordance with a number of tissue transplantation principles, such as the following:

(1) remove fat with a 12-gauge cannula for the best fat parcel size;

(2) avoid requiring fat cells from traveling long tube distances;

(3) maintain the suction at low or very low vacuum power (e.g., 8 to 12 inches of mercury);

(4) use transfer conduits having uniform internal diameters and use transfer conduits having internal diameters that are as large as mechanically feasible;

(5) avoid exposure of fat cells to air and light;

(6) avoid exposing the fat cells to water or saline;

(7) avoid vigorously mixing or shaking containers of donor fat cells while adding additives;

(8) filter out blood, serum, anesthetic, dead fat cells and triglycerides from removed fat tissue;

(9) treat removed fat tissue with additives to protect the liposite and potentially stimulate angiogenesis using additives such as growth hormone, platelet rich plasma, albumin and others;

(10) collect, treat, filter and reinject donor fat without removing the collected fat tissue from the original collection chamber;

(11) do not centrifuge collected tissue unless filtration is unsuccessful;

(12) avoid manipulating the fat in any way, such as by stirring or scraping off of a filter;

(13) maintain meticulous antisepsis during procedure;

(14) reinject the donor fat with as large a needle as is clinically feasible, and having an internal diameter that is as close to the internal diameter of the syringe outlet as possible; and

(15) reinject the fat tissue under the lowest possible power.

Although such principles do not all need to be followed in connection with a particular device or method in accordance with embodiments of the present invention, adhering to some or all of them can promote the successful transplantation of tissue.

Figure 1:
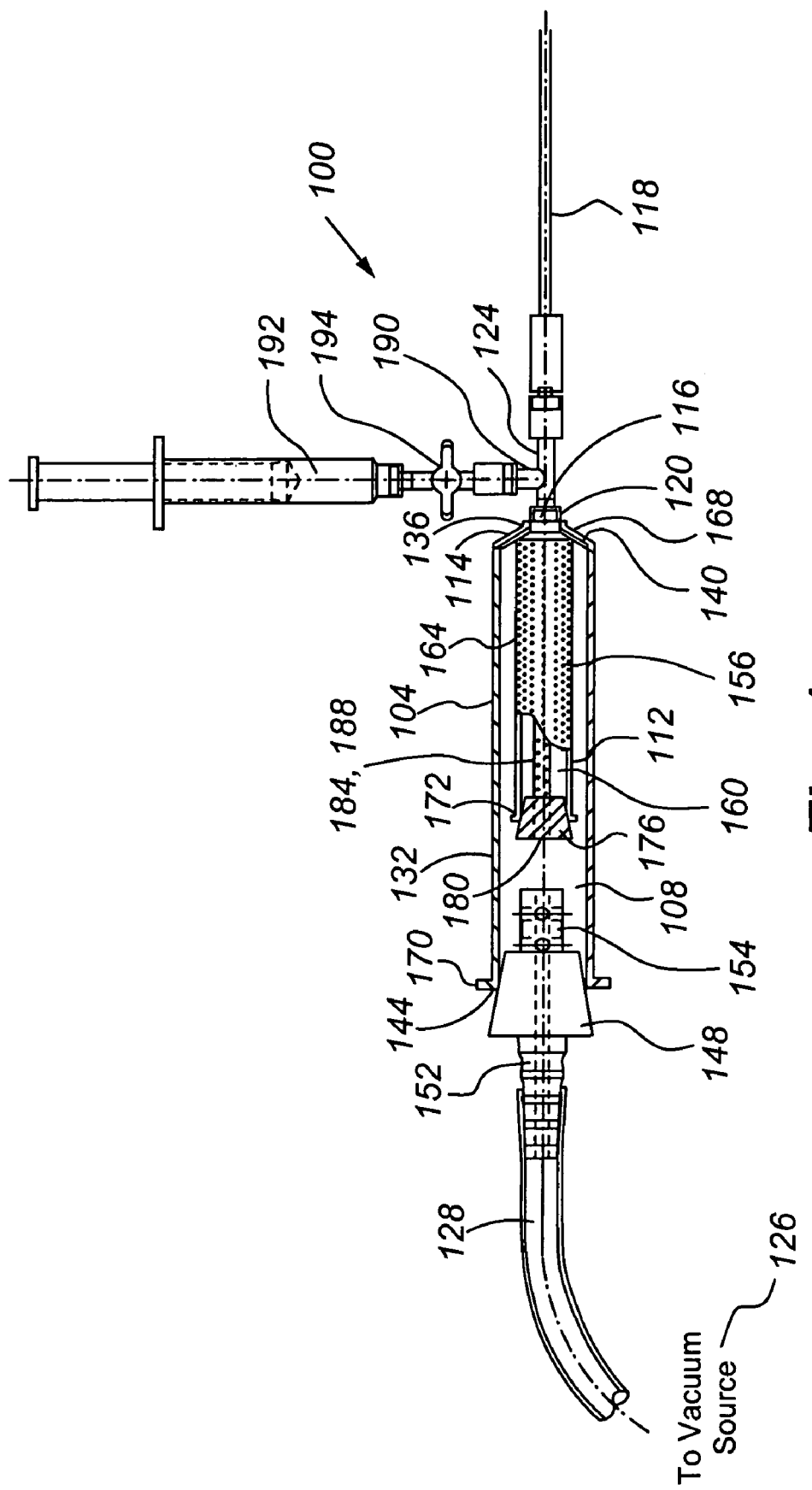
FIG. 1 is a cross-section of a device for tissue transplantation in accordance with embodiments of the present invention.

With reference now to FIG. 1, a tissue transplantation device 100 in accordance with embodiments of the present invention is depicted in cross-section. In general, the device 100 includes an outer chamber 104 defining an interior volume 108 sized to accommodate a perforated inner chamber 112. The device 100 additionally includes a cannula or needle 116 interconnected to an inlet 120 of the inner chamber 112, either directly or through an intermediate conduit 124. The interior volume 108 of the outer chamber 104 is placed in communication with a vacuum source 126 via a suction or vacuum line 128.

In accordance with embodiments of the present invention, the outer chamber 104 includes a substantially rigid body portion 132. As used herein, in connection with at least the outer chamber body 132, substantially rigid means that the outer chamber body 132 is capable of maintaining the interior volume 108 while a vacuum is established within the interior volume 108. For example, the outer chamber body 132 may be capable of maintaining the interior volume 108 while a vacuum of about 8 to 12 inches of mercury is established in the interior volume 108. Accordingly, the interior volume 108 can be operative as a vacuum chamber. In accordance with further embodiments of the present invention, the outer chamber body 132 may be rigid enough to allow a surgeon to use the outer chamber 104 as a handle while manipulating an attached or interconnected cannula 116 in connection with the removal of tissue from a donor site. In accordance with still further embodiments of the present invention, the outer chamber body 132 may be formed from a transparent or semitransparent material, to allow the perforated inner chamber 112 within the interior volume 108 to be viewed. In addition, the outer chamber body 132 of embodiments of the present invention such as illustrated in FIG. 1 may be generally cylindrical, and the interior volume 108 may comprise a generally cylindrical bore.

At a distal end 114, the outer chamber 104 may include an inlet 136 adapted to receive an inlet 168 of the inner chamber 112. Furthermore, in accordance with embodiments of the present invention, the inlet 136 may comprise a hole having a diameter such that it can receive the distal end 116 of the perforated inner chamber 112 in close fitting contact. A gasket 140 may also be provided at the distal end of the outer chamber 104 to assist in preventing vacuum leaks at the interface between the outer chamber inlet 136 and the inner chamber inlet 168.

The outer chamber 104 may additionally feature an open proximal end 144. During the aspiration of tissue, the proximal end 144 of the outer chamber 104 may receive a tapered plug 148. The plug 148 seals the open end 144 of the outer chamber 104, and may provide a tube 152 comprising a nipple, tapered stub or other fitting to which the suction tubing 128 can be interconnected, thereby permitting the interior volume 108 of the outer chamber 104 to be interconnected to a vacuum source 126. The tube 152 may optionally comprise or be associated with an end plug filter 154 to prevent some or all of the material drawn off of collected fat tissue from passing to the suction tube 128 and the vacuum source 126. Alternatively or in addition, filters may also be provided between the end plug 148 and the vacuum source 126. If provided, a filter 154 or other filter may comprise various filter arrangements and media, including perforated tubes, absorbent foams and gauzes, cartridges containing particulate filtration media, and/or other filtration media and structures. In accordance with further embodiments of the present invention, the tapered plug 148 may be removable, to permit access to the interior volume 108 of the outer chamber 104. In accordance with embodiments of the present invention, the tapered plug 148 may comprise a silicone or rubber material, with a tube 152 formed from metal or a polymer. Furthermore, it should be appreciated that the plug 148 need not be tapered. For example, the plug 148 can comprise a cap or an insert having threads that can interconnect with mating threads on the outer chamber body 132, the plug 148 can have a constant diameter for fitting in or over a mating surface formed as part of the outer chamber body 132, or can be formed in some other way to seal the proximal end 144 of the outer chamber 104.

The inner chamber 112 includes a substantially cylindrical body portion 156 having a substantially cylindrical interior bore 160. More particularly, the inner chamber body portion 156 is substantially cylindrical in that it does not feature projections, so that an inner chamber sleeve 304 can be accommodated, as will be described in greater detail elsewhere herein. Furthermore, the body portion 156 may be substantially rigid. As used herein in connection with at least the inner chamber body portion 156, substantially rigid means the cylindrical body portion 156 maintains its shape while tissue is collected within the interior bore 160 and while collected tissue is being forced from the interior bore 160. Furthermore, because the body portion 156 is substantially rigid, it can function as the body of a syringe, as described in greater detail described herein. In addition, a plurality of perforations 164 are formed in the cylindrical body 156. At the distal end 116 of the inner chamber 112, an inlet 168 is provided. The inlet 168 may provide surfaces for being received by the inlet 136 of the outer chamber 104 and/or the gasket 140, so that a seal is maintained at the interface between the outer chamber inlet 136 and the distal end 116 of the inner chamber 112. In addition, the fitting between the outer chamber inlet 136 and the inlet 168 of the inner chamber 112 can secure the inner chamber 112 with respect to the outer chamber 104 while tissue is being aspirated from a donor site. Accordingly, the interface between the inlet 136 of the outer chamber 104 and the inlet 168 of the inner chamber 112 may comprise a friction fitting, or a mechanical lock, such as may be provided by cooperating threads or other mechanical arrangement. In addition, the inlet 168 of the inner chamber 112 may provide a fitting for receiving a cannula or needle 118, and/or an intermediate conduit 124. Accordingly, exemplary embodiments of an inner chamber 112 may comprise an inlet 168 that provides the male portion of a luer connector. In accordance with embodiments of the present invention, no protrusions or flanges extend from the area of the body portion 156 and/or the area of the interior bore 160 in which the perforations 164 are formed. However, a flange or handle 170 may be provided, for example to assist in using the inner chamber 112 as the body of a syringe, as described herein.

The inner chamber body 156 may include an open proximal end 172. During the aspiration of tissue, the proximal end 172 may be sealed by a plug 176. In accordance with embodiments of the present invention, the plug 176 may have a center bore 180 that can house either an absorbent stick 184 or a perforated central suction tube 188. Where an absorbent stick 184 is provided, the stick may be formed from a compressed stick of polyvinyl alcohol (PBA) foam to aid in the absorption of residual oils from collected fat. In accordance with embodiments of the present invention, the stick is disposed of after use. The absorbent stick 184 may extend into the interior volume of the inner chamber 112, for example to almost the inlet 168 at the distal end 116 of the inner chamber 112. In connection with embodiments where a perforated central suction tube 188 is provided, suction created by placing the interior volume 108 of the outer chamber 104 in communication with a vacuum source can be used to draw material from collected fat from the center of the collected fat specimen. The perforations 190 in the central suction tube 188 may be sized and arranged like the perforations 164 in the inner chamber 112 body 156. The central suction tube 188 may extend almost to the inlet 168 at the distal end 116 of the inner chamber 112. An absorbent stick 184 may also be combined with a suction tube. In accordance with embodiments of the present invention, the plug 176 may be formed from a polymer and may be tapered to seal the open end 172 of the inner syringe 112. Alternatively, the plug 112 may be threaded to interconnect to mating threads provided as part of the inner chamber 112, or to interconnect and seal the proximal end of inner chamber 112 through some other arrangement.

Embodiments of the present invention may provide an intermediate conduit 124 for interconnecting the cannula 118 to the inlet 168 of the inner chamber 112. As used herein, the term cannula may include needles. Specifically, a needle is a particular type of cannula, in that it refers to a relatively small cannula. Furthermore, the conduit 124 may comprise an inlet branch 190 for selectively interconnecting a fluid reservoir 192 to the conduit 124 through a stopcock 194. Accordingly, embodiments of the present invention may allow a fluid, for example an additive or tissue treatment fluid, to be introduced or instilled in tissue as that tissue is collected and drawn through the conduit 124 to the inner chamber 112. In accordance with embodiments of the present invention, the fluid reservoir 192 can comprise a syringe.

As can be appreciated by one of skill in the art from the description provided herein, when operatively assembled and configured for the removal of tissue from a donor site, a device 100 allows tissue to be aspirated through a cannula 118 by interconnecting the device 100 to a vacuum source 126. Tissue collected through the cannula 118 is passed through a conduit 124, if provided, and into the interior bore 160 of the inner chamber 112. In accordance with embodiments of the present invention, the inner canal of the cannula 118, a conduit 124, and the inlet 168 of the inner chamber 112 are substantially uniform and as large as mechanical feasible. Such an arrangement helps to prevent the damage that can be caused by forcing aspirated fat through narrow conduits and changes in conduit size.

The fat drawn into the interior bore 160 of the inner chamber 112 is collected in the inner chamber 112, while blood, serum, anesthetic agents and/or other materials are drawn through the perforations 164, and into the interior volume 108 of the outer chamber 104 by the vacuum introduced through the tube 152. The materials drawn off of the fat may additionally include additive introduced from a reservoir 192 to the flow of tissue through the conduit 124, or drawn into the inner chamber 112 from a reservoir 192 after tissue has been collected in the inner chamber 112. The materials drawn off of the collected fat may be collected by filters, for example in-line with the vacuum line 128 or provided as part of the vacuum source 126, to prevent such material from reaching the pump mechanism of the vacuum source 126. Accordingly, separation of collected fat from other, unwanted materials, can be effected without removing the collected fat from the inner chamber 112. In addition, separation of the collected fat from other materials can be effected without requiring centrifuging.

With reference now to FIG. 2, a detail of the relationship between the inlet 136 of the outer chamber 104 and the inlet 168 of the inner chamber 112 is shown. In particular, it can be seen that the inlet 168 of the inner chamber 112 may, in accordance with embodiments of the present invention, comprise the male portion of a slip type luer connector 204. According to other embodiments, the inlet 168 can comprise a lock type luer connector or other fitting. In addition, it can be seen that the inlet 168 may include a barrel portion, for example as part of the luer connector 204, that is in close fitting contact with the opening of the outer chamber inlet 136, when the inner chamber 112 is inserted into the interior volume 108 of the outer chamber 104 such that the inlet 168 of the inner chamber 112 protrudes from the inlet 136 of the outer chamber 104. FIG. 2 also shows that the distal end 116 of the inner chamber 112 may include a tapered or dished surface 208 having an angle that is equal or complementary to a tapered surface 212 at the distal end 114 of the outer chamber 104, and that the tapered surfaces 208, 212 can hold the gasket 140 between them, to form a seal between the inlet 168 of the inner chamber 112 and the inlet 136 of the outer chamber 104.

With reference now to FIG. 3A, an inner chamber 112 in accordance with embodiments of the present invention is illustrated. In addition, an inner chamber sleeve 304 is shown. In accordance with embodiments of the present invention, the perforations 164 in the body portion 156 of the inner chamber 112 do not extend along at least a first area or portion 308 of the inner chamber body 156. In addition, the inner chamber sleeve 304 may include a slit 312. Accordingly, the inner chamber sleeve 304 may be formed so that it has a diameter that is slightly smaller than the outside diameter of the body 156 of the inner chamber 112. Therefore, when the inner chamber sleeve 304 is slipped over the body 156 of the inner chamber 112, it can tightly cover the perforations 164, and the slit 312 can be registered with the portion 308 along which no perforations 164 are formed. As can be appreciated by one of skill in the art after appreciation of the disclosure provided herein, the inner chamber sleeve 304 may be positioned to cover the perforations 164 in the inner chamber 112 when the inner chamber 112 has been removed from the outer chamber interior volume 108, in preparation for the reinjection of collected tissue. In accordance with other embodiments of the present invention, the inner chamber sleeve 304 may be sized so that it can be received within the interior bore of the inner chamber 112 to close off the perforations 164 from the inside of the inner chamber 112. Furthermore, embodiments of the present invention do not require that a slit 312 be formed in the inner chamber sleeve 304.

Figure 3B:
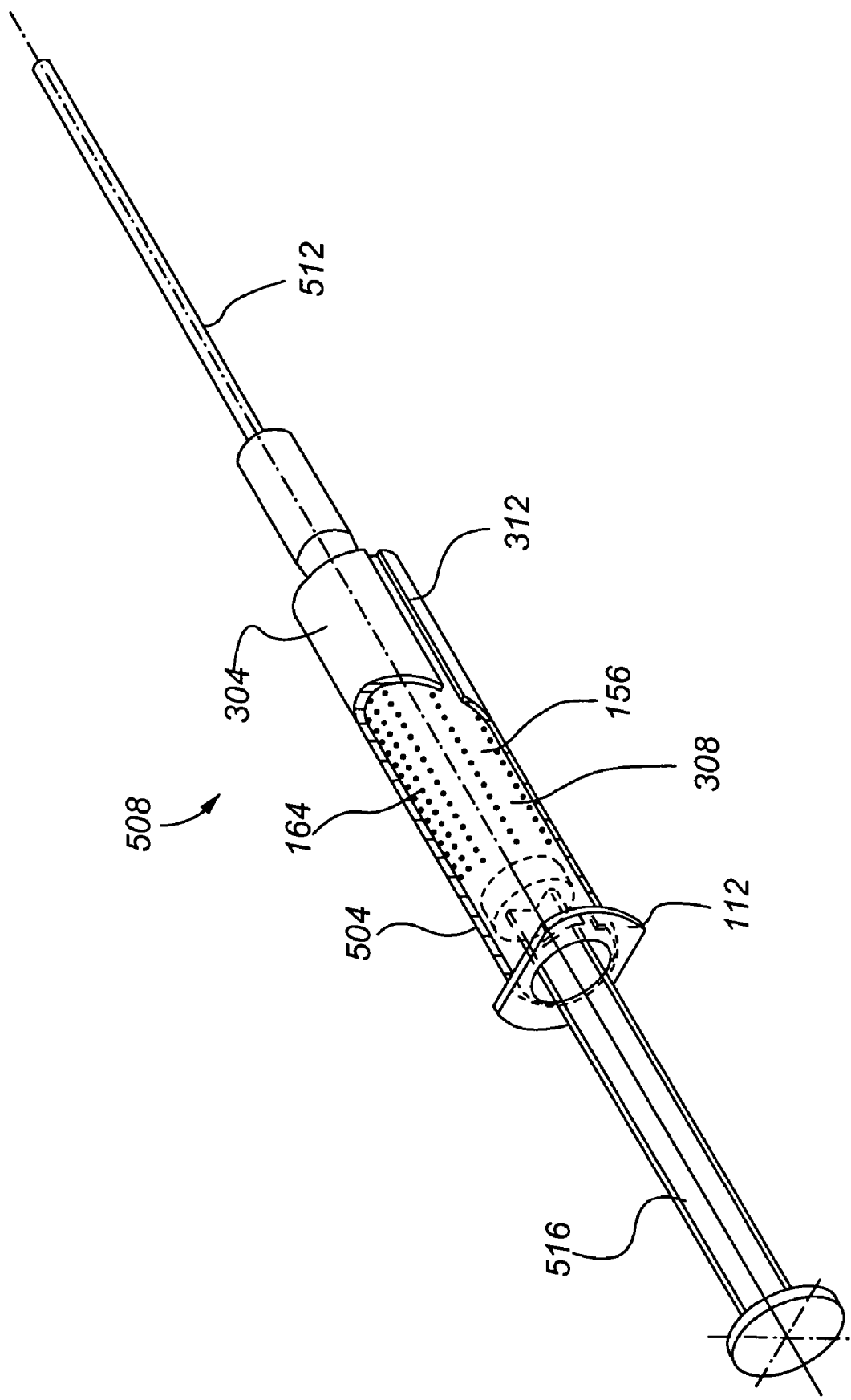

With reference now to FIG. 3B, an inner chamber 112 with an inner chamber sleeve 304 positioned over the body 156 of the inner chamber 112 is illustrated. Furthermore, the inner chamber sleeve 304 is shown partially cut away to illustrate that the perforations 164 have been covered by the inner chamber sleeve 304 such that the inner chamber 112 can comprise the body 504 of a syringe 508 consisting of the body 504, a reinjection cannula or needle 512 and a plunger 516. In addition, FIG. 3B illustrates the positioning of the slit 312 in the inner chamber sleeve 304 over the portion 308 of the inner chamber body 156 in which no perforations 164 are formed.

In accordance with other embodiments of the present invention, and with reference now to FIGS. 3C and 3D, the inner chamber sleeve 304 may itself be provided with a plurality of perforations 316. Furthermore, the perforations 316 may be arranged such that they register with corresponding perforations 164 in the inner chamber 112 (see FIG. 3C). Accordingly, the inner chamber sleeve 304 can be positioned such that the interior of the inner chamber 112 is in communication with the exterior of the inner chamber through the perforations 164 and 316, for example to collect tissue in the inner chamber 112 using a vacuum formed in the interior volume 108 of the outer chamber 104. FIG. 3C therefore illustrates an inner chamber 112 and an inner chamber sleeve 304 configured for the collection of tissue in accordance with embodiments of the present invention. By rotating or otherwise moving the inner chamber sleeve 304 with respect to the inner chamber 112, such that the perforations 164 in the inner chamber are not registered with the perforations 316 in the inner chamber sleeve 304, the perforations 164 can all be sealed, for example to reinject tissue collected in the inner chamber 112 into a body (see FIG. 3D). The inner chamber 112 and the inner chamber sleeve 304 can then be associated with a reinjection cannula or needle 512 and a plunger 516, as shown in FIG. 3D, for reinjecting collected tissue.

Figure 4:
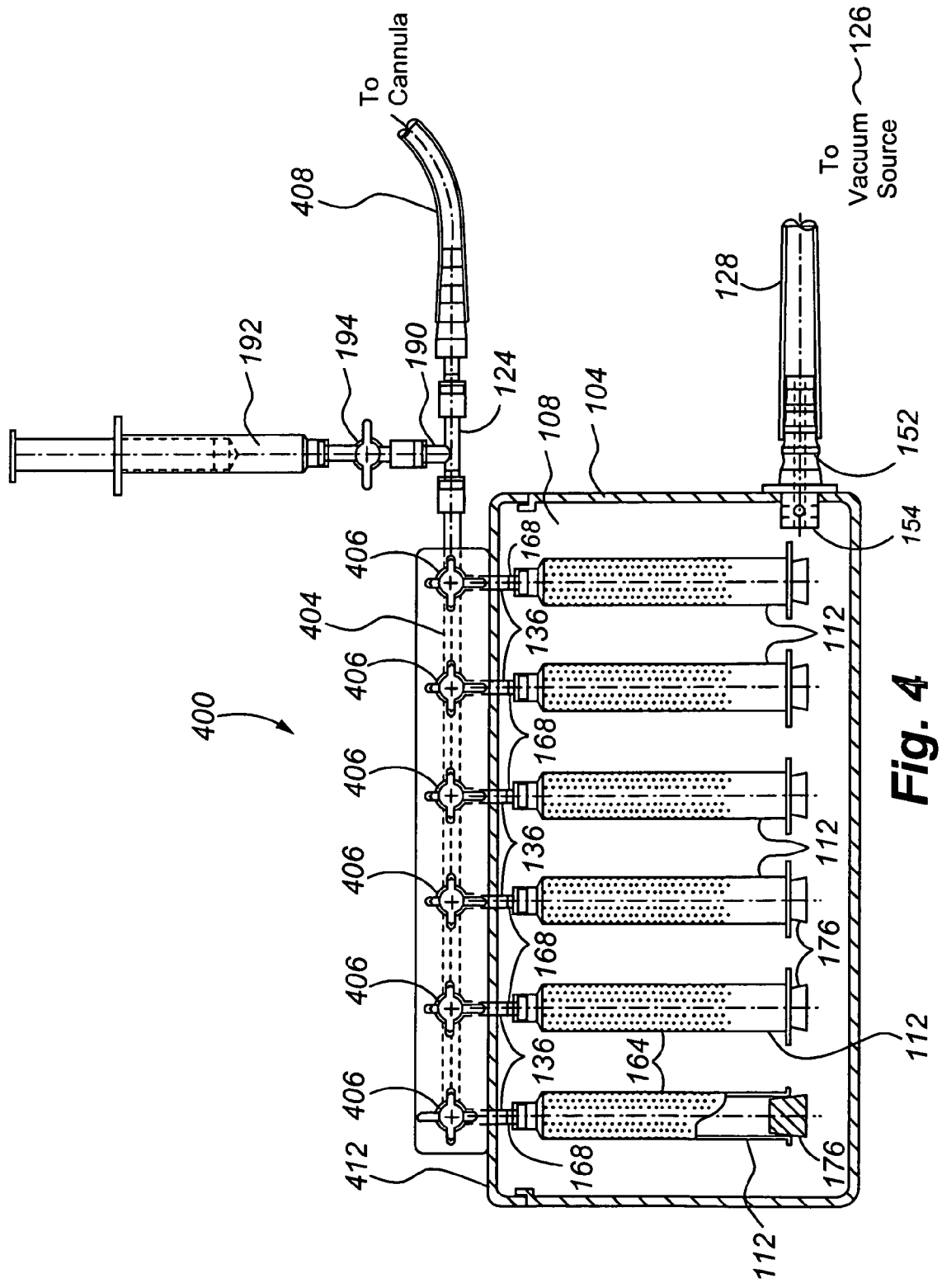
FIG. 4 is a cross-section of a device for tissue transplantation having multiple perforated inner chambers in accordance with embodiments of the present invention.

With reference now to FIG. 4, a tissue transplantation device 400 having multiple inner chambers 112 in accordance with embodiments of the present invention is depicted. As shown in FIG. 4, such embodiments may feature an outer chamber 104 having an interior volume 108 that is sufficiently large to house a number of inner syringes 112. According to such an embodiment, a manifold 404 is provided for delivering collected tissue to the inner chambers 112. An inlet 136 may be provided for each inner chamber 112, to interconnect the inner chambers 112 to the manifold 404. In accordance with embodiments of the present invention, the inlets 136 may comprise the female portion of a slip or lock type luer connector, such that the inlet 168 of an inner chamber 112 comprising the male portion of a corresponding luer connector can be securely received. In accordance with further embodiments of the present invention, the manifold 404 may be provided with stopcocks 406, to allow tissue to be collected in a selected inner chamber or chambers 112. In addition, by providing stopcocks 406, the device 400 can be used even if all of the inlets 136 associated with the manifold 404 are not connected to an inner syringe 112. Although the provision of stopcocks 406 in association with the manifold 404 can provide certain advantages, it should be appreciated that they are not required. In addition, a flexible tissue collection conduit 408 is provided for interconnecting the device 400 to a cannula.

In order to permit access to the inner volume 108, for example to insert an inner chamber 112, to remove one or more of the inner chambers 112 after the inner chambers 112 are full of collected tissue, or to clean the interior volume 108, the outer chamber 104 may be provided with an access panel or lid 412. As shown in FIG. 4, the access panel or lid 412 may incorporate or be attached to the manifold 404. Alternatively, a panel or lid 412 separate from the manifold 404 may be movable or removable to permit access to the interior volume 108 of the outer chamber 104.

As also illustrated in FIG. 4, the outer chamber 104 may generally be in the form of a box or other shape sized and arranged to contain a desired number of inner chambers 112. In addition, the outer chamber 104 of such an embodiment is substantially rigid so that a vacuum, for example a slight vacuum of about 8-12 inches of mercury, can be maintained within the interior volume 108 without collapsing the outer chamber 104. The outer chamber 104 may be formed from a transparent or translucent material, in whole or in part, to permit the amount of tissue collected in the inner chambers 112 to be viewed from outside of the outer chamber 104.

The outer chamber may additionally include a fitting or tube 152 having a tapered end, a nipple or other fitting to place the interior volume 108 in communication with a vacuum source 126 via a section of suction tubing 128. The tube 152 may optionally comprise or be associated with a filter 154 to collect fluids and other material drawn off of fat collected in the inner syringes.

In addition, embodiments of the present invention may provide an intermediate conduit 124 that provides an inlet 190 for fluid provided by fluid reservoir 192 in order to instill an additive or other fluid to tissue being drawn through the intermediate conduit 124 and/or to tissue that has been collected in the inner chambers 112. In accordance with embodiments of the present invention, the fluid reservoir 192 may comprise a syringe. A stopcock 194 may be provided between the fluid reservoir 112 and the fluid conduit 124.

Figure 5A:
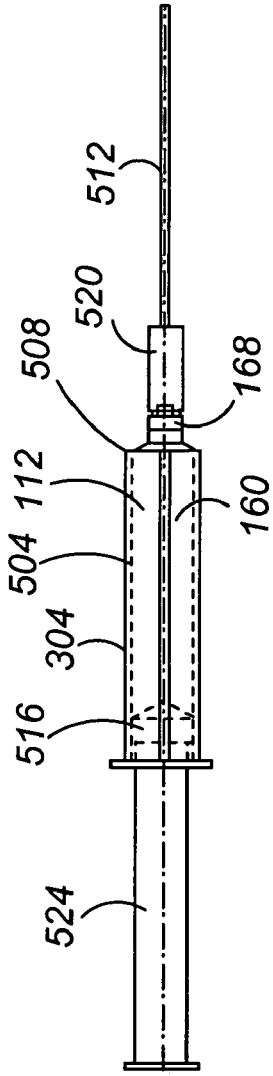
FIGS. 5A-5C are side elevations of an inner chamber configured for the reinjection of tissue in connection with exemplary reinjection apparatuses, in accordance with embodiments of the present invention.
Figure 5B:
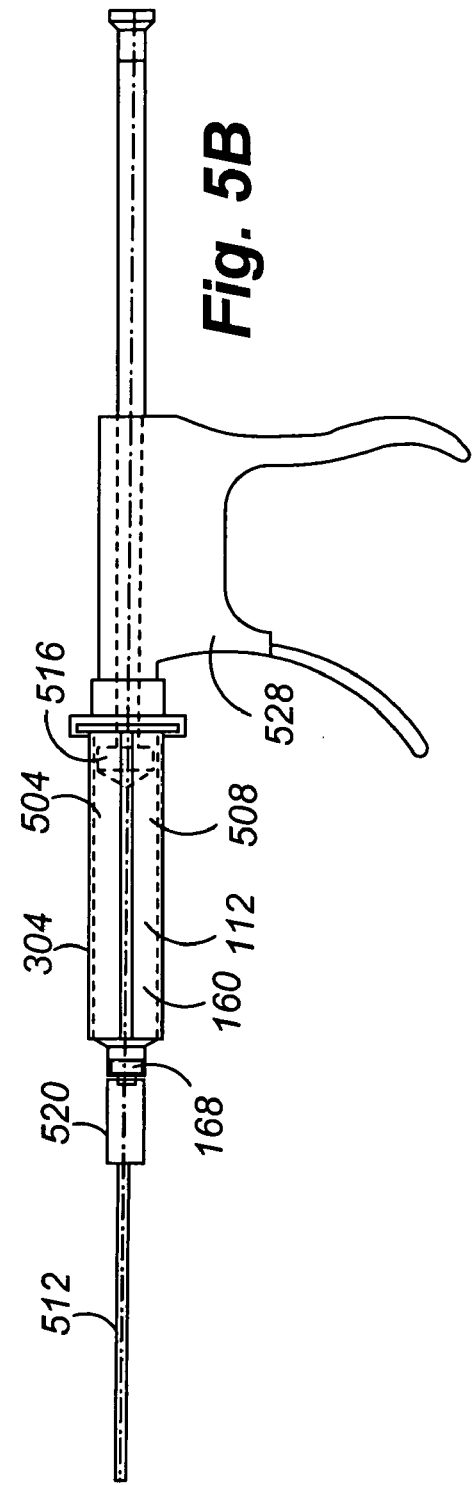
Figure 5C:
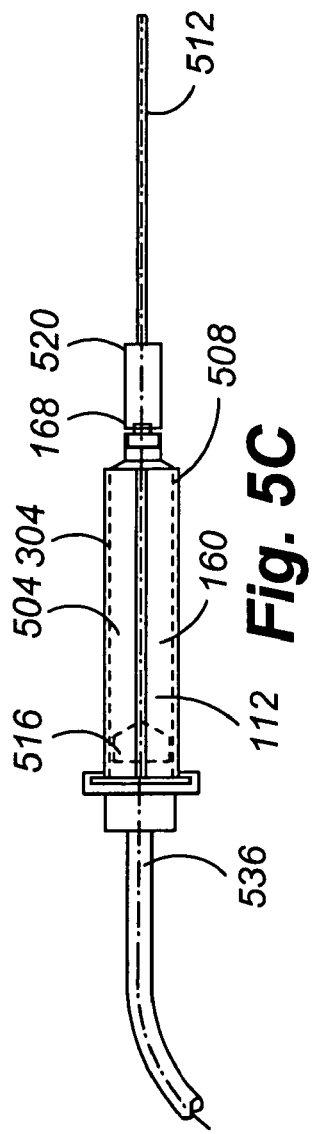

With reference now to FIGS. 5A-5C, various embodiments of an inner syringe 112 configured for reinjecting collected tissue into a body are illustrated. In connection with each of the illustrated configurations, the inner syringe 112 is shown with an inner chamber sleeve 304 covering the perforations 164 in the inner syringe 112. Accordingly, the inner chamber 112 and inner chamber sleeve 304 combine to form the body 504 of a syringe 508. The syringe 508 also includes a reinjection cannula or needle 512 and a plunger 516 inserted into the interior bore 160 of the inner chamber 112. As shown in FIGS. 5A-5C, the reinjection cannula 512 may be interconnected to an inner chamber inlet 168 comprising the male portion of a luer connector by a body member 520 comprising the female portion of a luer connector.

With particular reference now to FIG. 5A, the inner chamber 112 is incorporated into a syringe 508 comprising a conventional manual syringe with a thumb operated plunger arm 524. The manual syringe may also comprise handles to provide a control syringe. In FIG. 5B, the inner chamber 112 is shown incorporated as part of a syringe 508 operated by a mechanical ratchet plunger 528. In FIG. 5C, the inner chamber 112 is shown as part of a syringe 504 interconnected to a compressed air type injection device 536. In connection with a compressed air device, the operator can selectively allow compressed air to force the plunger 516 against tissue collected in the inner syringe 112, to reinject that tissue into a body.

As can be appreciated by one of skill in the art after consideration of the description provided herein, fat collected in an inner chamber 112 does not need to be removed from the inner chamber 112 until it is reinjected into a body. In order to configure the inner syringe 112 for reinjection of collected tissue, an inner chamber sleeve 304 is positioned such that the perforations 164 in the body 156 of the inner chamber 112 are blocked. In connection with embodiments incorporating an inner chamber sleeve 304 that slips over the outside of the inner chamber 112, blocking the perforations 164 may comprise inserting the body 156 of the inner chamber 112 into the sleeve 304. In accordance with embodiments utilizing an inner chamber sleeve 304 adapted for insertion within the interior bore 160 of the inner chamber 112, the inner chamber sleeve 112 is slipped into the interior volume 160, separating the collected tissue from the perforations 164 in the wall of the inner chamber body 156. In accordance with embodiments of the present invention utilizing an inner chamber sleeve 304 that includes perforations 316, configuring the inner chamber 112 for the reinjection of tissue may comprise rotating the inner sleeve 304 from a position in which the provided holes 316 register with the perforations 164, to a position such that the holes 316 are out of registration with the perforations 164, and the perforations 164 are therefore blocked.

In addition, the inlet 168 of the inner chamber 112 is interconnected to a reinjection cannula 512, the end plug 176 is removed from the proximal end 172 of the inner chamber 112, and a plunger 516 is inserted into the interior bore 160 of the inner chamber 112 through the open proximal end 172. The syringe 504 thus formed using the inner chamber 112 is then ready for manual reinjection of tissue, or for association with an injection device for use in connection with reinjection.

Figure 6:
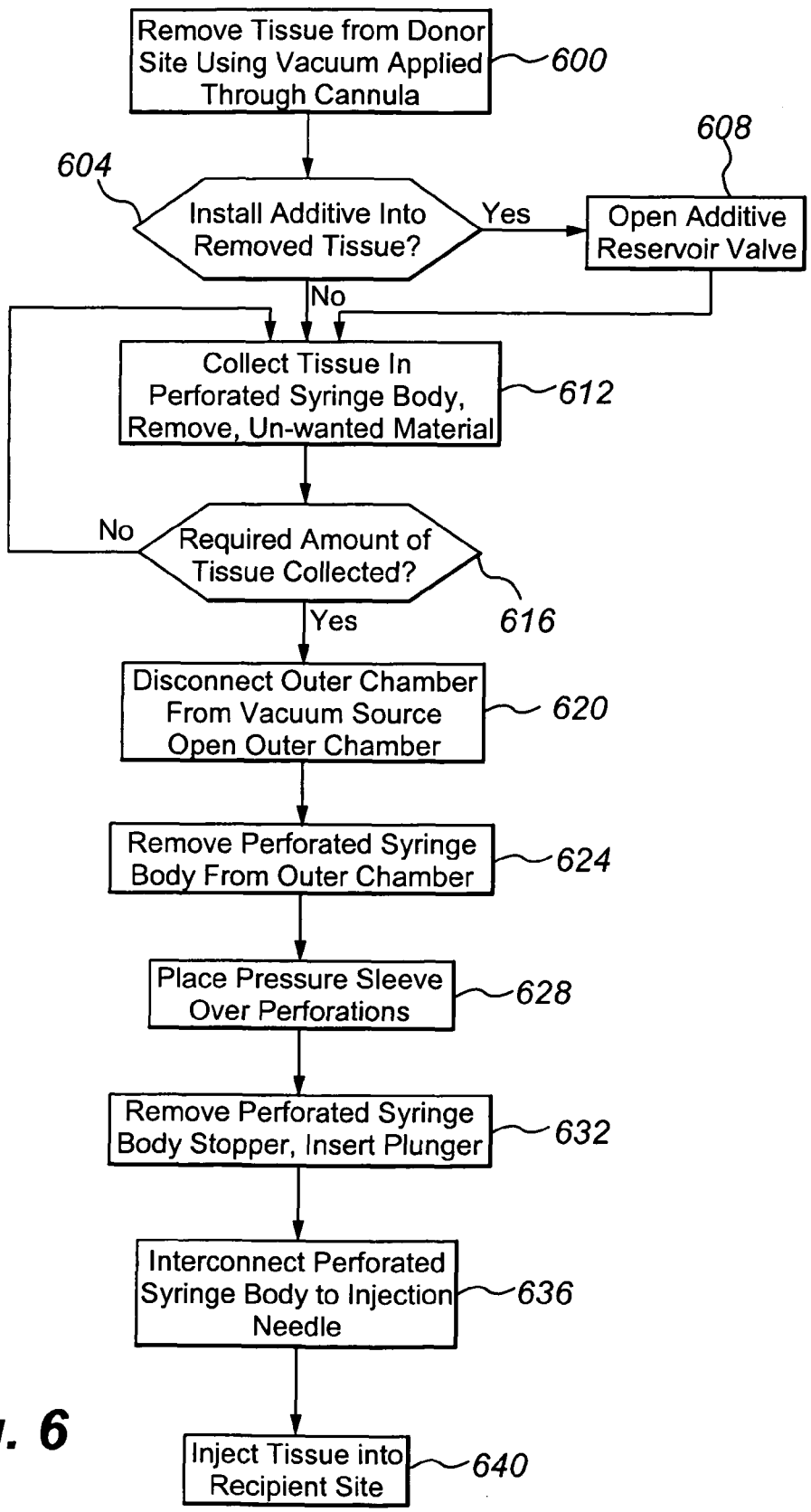
FIG. 6 is a flowchart depicting aspects of a method for transplanting tissue in accordance with embodiments of the present invention

With reference now to FIG. 6, aspects of a method for transplanting tissue in accordance with embodiments of the present invention are illustrated. Initially, at step 600, tissue is removed from a donor site using a vacuum applied to that site through a cannula 116. In accordance with embodiments of the present invention, a vacuum of about 8 to 10 inches of mercury is applied using a vacuum source 126. At step 604, it can be determined whether an additive or other fluid is to be instilled into the removed tissue. If an additive or other fluid is to be instilled into the removed tissue, the fluid can be introduced to the flow of collected tissue. That is, the fluid can be instilled while the tissue flows through the intermediate conduit 124. In connection with adding the fluid, a stopcock or valve 194 controlling communication between a fluid reservoir 192 and the intermediate conduit 124 can be opened (step 608). In addition, a plunger provided as part of the fluid reservoir 192 can be manipulated to provide additional control to the amount of fluid introduced to the flow of tissue. Alternatively or in addition, an additive or other fluid can be instilled in collected tissue after collection.

The removed tissue is collected in the perforated inner chamber body 156, and unwanted materials removed from the collected fat through the provided perforations 164 (step 612). As can further be appreciated, the unwanted materials tend to be drawn from the interior bore 160 of the inner chamber 112 and towards the tube 152 and the vacuum conduit 128.

At step 616, a determination may be made as to whether the required amount of tissue has been collected (step 616). If the required amount of tissue has not been collected, the process may return to step 612.

Once the required amount of tissue has been collected, the outer chamber 104 can be disconnected from the vacuum source 126, and the outer chamber 104 can be opened (step 620). In connection with an embodiment of the present invention such as illustrated in FIG. 1, disconnecting the outer chamber 104 from the vacuum source 126 and opening the outer chamber 104 may comprise removing the plug 148 from the proximal end of the outer chamber body 132. In connection with a device 400 such as illustrated in FIG. 4, disconnecting the outer chamber 104 from the vacuum source 126 may comprise turning off the vacuum source 126 and opening the outer chamber 104 may comprise opening an access panel 412. After opening the outer chamber 104, the inner chamber 112 may be removed from the interior volume 108 of the outer chamber 104 (step 624).

After the inner chamber 112 is removed from the outer chamber, a pressure or inner chamber sleeve 304 may be positioned over the perforations 164 in the body 156 of the inner chamber 112 (step 628). Positioning an inner chamber sleeve 304 over the perforations 164 may comprise sliding the sleeve 304 over an exterior of the inner chamber 112, such that the perforations 164 are covered. Alternatively, placing a sleeve 304 over the perforations 164 may comprise sliding a pressure sleeve into the interior of the inner chamber 112. According to still other embodiments, placing the sleeve 304 over the perforations 164 may comprise rotating an inner chamber sleeve 304 having perforations 316 such that the perforations 316 of the sleeve 304 are out of registration with the perforations 164 in the inner chamber 112, blocking the perforations 164 in the inner chamber 112. Accordingly, placing an inner chamber sleeve 304 over the perforations 164 prevents communication between the interior bore of the inner chamber 112 and the exterior of the inner chamber through the perforations 164.

The stopper or plug 176 in the end of the inner chamber 112 may then be removed, and a plunger 516 (see e.g., FIGS. 5A-5D) may be inserted into the interior bore 160 of the inner chamber 112 (step 632). The inner chamber 112 thus can form the body of a syringe 508 and may be interconnected to a reinjection cannula 512 (step 636). The completed syringe 504 may then be used to reinject the removed tissue into a recipient site (step 640). Examples of techniques for reinjecting tissue include manual operation of the syringe 504, operation of a syringe using a mechanical ratchet type gun (e.g., as shown in FIG. 5B), and injection using a compressed air type injection device (e.g., as illustrated in F*ig*. 5C).

Figure 7:
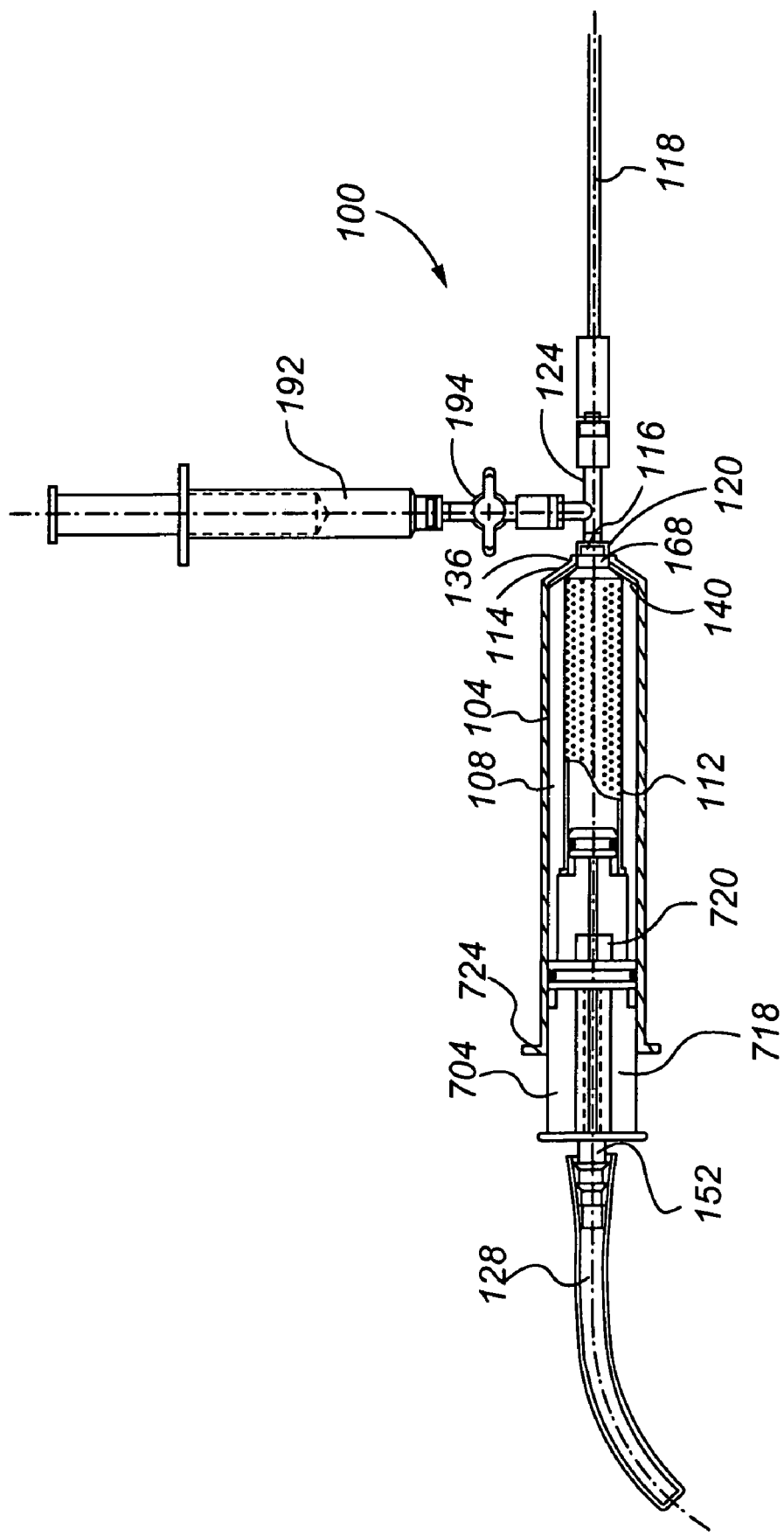
FIG. 7 is a cross-section of a device for tissue transplantation in accordance with other embodiments of the present invention.
Figure 8:
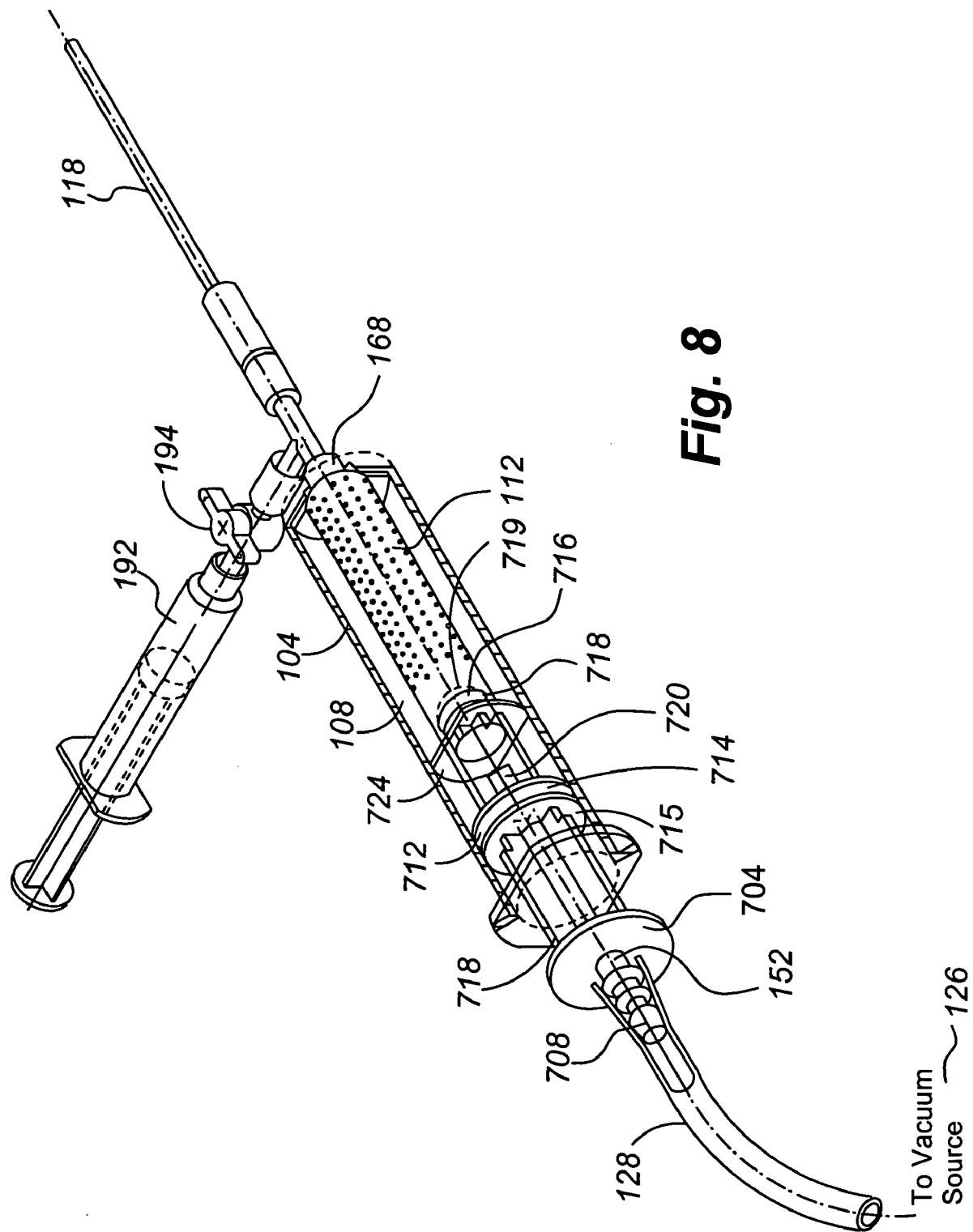
FIG. 8 is a partially cutaway perspective view of the device for tissue transplantation illustrated in FIG. 7.

In FIG. 7, a cross-section of a device 100 for tissue transplantation in accordance with other embodiments of the present invention is illustrated. In FIG. 8 the device 100 of FIG. 7 is shown in a partially cutaway perspective view. In general, the device 100 illustrated in FIGS. 7 and 8 includes an outer chamber 104 that defines an interior volume 108 sized to accommodate a perforated inner chamber 112. Accordingly, the device 100 illustrated in FIGS. 7 and 8 is, at least in certain respects, the same as or similar to the device 100 illustrated in FIG. 1. However, the device 100 illustrated in FIGS. 7 and 8 includes an integrated plug unit 704 in place of the separate plugs or stoppers 148 and 176 shown in FIG. 1. The integrated plug unit 704 generally includes an outer chamber seal 712 and in inner chamber seal 716. More particularly, the outer chamber seal 712 of the integrated plug unit 704 is received by the open proximal end 144 of the outer chamber 104, while the inner chamber seal 716 is received by the open proximal end 172 of the inner chamber 112. In accordance with embodiments of the present invention, the seals 712, 716 are each formed by an O-ring 714, 718 carried within a grooved disk 715, 719. In addition, the integrated plug unit 704 may include lateral walls 718 extending from the center axis of the integrated plug unit 704, to assist in maintaining the alignment of the integrated plug unit 704 with respect to the outer chamber 104.

The integrated plug unit 704 incorporates a tube 152 comprising a nipple, tapered stub or other fitting to which the suction tubing 128 can be interconnected. Furthermore, the tube 152 extends through the plug unit 704 from the proximal portion 708 interconnected to the suction tube 128 at least to an opening 720 between the outer chamber seal 712 and the inner chamber seal 716. Accordingly, through the opening 720, the interior volume 108 of the outer chamber 104 can be placed in communication with the vacuum source 126, allowing a vacuum to be created within the interior volume 108.

As shown in FIG. 8, the perforated inner chamber 112 of embodiments of the present invention may comprise a handle 724. Furthermore, the handle 724 can be sized such that portions of the handle 724 are in contact with the interior surface of the outer chamber 104, to assist in maintaining the alignment of the perforated inner chamber 112 with respect to the outer chamber 104. In particular, the handle 724 and the inlet 168 of the perforated inner chamber 112 may assist in maintaining the perforated inner chamber 112 and the outer chamber 104 in axial alignment.

The provision of an integrated plug unit 704 reduces the number of separate components that a user is required to handle in connection with using the tissue transplantation device 100, as compared to certain other embodiments. In addition, it can be appreciated that an integrated plug unit 704 can accommodate inner chambers 112 having different lengths by adjusting the distance that a plug unit 704 is inserted into the outer chamber 104.

With reference now to FIG. 9, a tissue transplantation device 100 in accordance with still other embodiments of the present invention is illustrated. In particular, the perforated inner chamber 112 is shown partially cut away to reveal a perforated central suction tube 188 extending from an integrated plug unit 704 into the interior of the inner chamber 112. The perforated central suction tube 188 may be interconnected to or integral with the integrated plug unit 704 of the embodiment in FIG. 9. Furthermore, the central suction tube 188 includes a closed distal end and an open proximal end that is in communication with the vacuum tube 128 through the tube 152. Accordingly, the central tube 152 in such embodiments extends through the inner chamber seal 716 such that a vacuum can be applied from the center portion of the perforated inner chamber 112, as well as from the outer diameter. In addition to the central suction tube 188, an opening 720 between the outer chamber seal 712 and the inner chamber seal 716 is provided to create a vacuum within the interior volume 108 of the outer chamber 104 around the exterior of the inner chamber body 156. In accordance with embodiments of the present invention, the perforated central suction tube 188 may include perforations 190 that are sized and arranged in the same or in a similar fashion as the perforations 164 in the body 156 of the inner chamber 112.

In accordance with embodiments of the present invention, a device 100 for transplanting tissue may comprise an outer syringe 104 in the form of a substantially rigid cylindrical tube or syringe body formed from a clear polymer, such as polypropylene acrylic or polycarbonate. Other example materials from which the outer chamber 104 can be formed include metal, ceramic, other polymers and glass. Although transparent materials are desirable because they allow the inner chamber 112 to be viewed, for example to determine when the inner chamber 112 is full, they are not required. In accordance with exemplary embodiments of the present invention, the capacity of the interior volume 108 of the outer container 104 may be from about 10 cc to about 100 cc. In accordance with still other embodiments of the present invention, the interior volume 108 or capacity of the outer chamber 104 is about 60 cc. The outer chamber 104 may additionally feature an inner diameter of from about 0.5 inches to about 2 inches. In accordance with further embodiments, the inner diameter of the outer chamber 104 is about 1 inch. The thickness of the outer syringe may, in accordance with embodiments of the present invention, range from about 0.0156 inches to about 0.250 inches, and is about 0.0625 inches in an exemplary embodiment. The proximal open end 144 may have an inside diameter of from about 0.5 inch to 1.5 inch. In accordance with further embodiments, the open end 144 may have an inside diameter of about 1 inch. The plug 148 may have a central hole that is from about 0.065 inch to about 0.25 inch in diameter, which may extend for the entire length of the plug 148. In accordance with further embodiments, the plug 148 may have a central hole that is about 0.125 inch in diameter. The distal 114 or inlet 136 end of the outer chamber 104 may include a center hole that is from about 0.21 to about 0.5 inches in diameter. In accordance with embodiments of the present invention, the center hole at the inlet 136 of the outer chamber 104 is about 0.37 inch. Furthermore, the inlet 136 is configured to allow the inlet 168 of the inner chamber 112 to exit the interior volume 108 of the outer chamber 104.

In accordance with embodiments of the present invention in which a plurality of inner chambers 112 can be simultaneously contained within the interior volume 108 of the outer chamber 104, such as illustrated in FIG. 4, the outer chamber 104 may be generally in the form of a box. Examples of materials from which the outer chamber 104 of such embodiments can be formed include clear or translucent acrylic or clear or translucent polymer. Other materials suitable for forming the outer chamber or box 104 in embodiments containing multiple inner chambers 112 include glass, translucent polymers, opaque polymers, and other clear polymers. Although not necessary, a transparent material is desirable in order to allow the amount of tissue that has been collected in the inner chambers 112 to be viewed. In accordance with an exemplary embodiment, the box is from about 2 to 10 inches high, 6 to 12 inches long, and 4 to 12 inches deep. In a further exemplary embodiment, the box is about 8 inches high, about 8 inches long, and about 6 inches deep. In addition, the outer chamber 104 is air tight and includes a resealable lid or access panel 412. The wall thickness of the outer chamber 104 may range from about 0.1 inch to about 0.25 inch, and in accordance with an exemplary embodiment of the present invention wall thickness is about 0.125 inch. Furthermore, the material and thickness should be selected so that the outer chamber 104 does not collapse as a result of the creation of a vacuum within the inner volume 108. In accordance with still other embodiments, the outer chamber 104 may be configured to hold any number of inner chambers 112. For example, the outer chamber 104 can be configured to contain 6 inner chambers 112. Furthermore, individual stopcocks 406 can be provided in the manifold 404, for example where operation with less than a maximum number of inner chambers 112 is desired.

According to embodiments of the present invention, the inner chamber 112 is formed from clear or translucent polycarbonate polymers or acrylic. Other suitable materials include other glass. As an example, the interior volume of the inner syringe 112 may be from about 0.25 cc to about 60 cc. In accordance with embodiments of the present invention, the interior volume of the inner chamber 112 is about 10 cc. The inlet 168 may comprise a slip or lock type luer connector having an internal diameter from about 0.05 inches to about 0.25 inches. In accordance with embodiments of the present invention, the internal diameter of the luer connector may be about 0.07 inches.

The perforations 164 may each have a diameter from about 0.015 inches to about 0.03 inches. In accordance with certain embodiments, the perforations 164 may have a diameter of about 0.02 inches. The perforations 164 may be arranged such that there are from about 75 to 150 holes per square inch. In accordance with other embodiments, the holes or perforations 164 may be arranged such that there are 86.8 holes per square inch. Furthermore, the total number of perforations 164 may range from about 300 to about 500 perforations 164 in an inner chamber 112 having a capacity of about 10 cc. In accordance with further embodiments, an inner chamber 112 having a capacity of about 10 cc may have about 350 perforations 164. Furthermore, the filter area provided by the inner chamber 112 may be from about 4 to about 5 inches for a 10 cc capacity inner chamber 112. As a particular example, the filter area of an inner chamber 112 having a 10 cc volume may be about 4.3 square inches.

The length of the inner chamber 112 may range from about 2 inches to about 10 inches. In a particular example, the inner syringe has a length of about 4 inches. The diameter of the inner chamber 112 may be from about 0.1 inches to 1.5 inches. In a particular example, the diameter of the inner chamber 112 is about 0.5 inches. As noted above, the capacity of the inner chamber 112 may be about 10 cc. In accordance with other embodiments, the capacity of the inner chamber 112 may range from about 0.25 cc to about 60 cc.

If provided, an inner chamber 112 inner suction tube 188 may be formed from polymer, glass, metal or ceramic material, and the bore in the end plug 176 places in the interior of the interior of the inner suction tube 188 in communication with the interior volume 108 of the outer chamber 104. In accordance with embodiments of the present invention, the inner tube 188 may have a length that is about 90 percent of the length of the inner syringe, plus or minus 5 percent. In accordance with other embodiments, the inner collection tube 188 may extend into the interior volume of the inner chamber 112 for a distance equal to about 0 percent to about 90 percent of the length of the inner chamber body 156. The diameter of the suction line 128 may range from about 0.075 to about 0.55 inches. In an exemplary embodiment, the diameter of the inner tube is about 0.125 inches. The diameter of the holes or perforations in the tube 188 may range from about 0.015 to about 0.03 inches. In a particular embodiment, the collection tube 188 contains 30 holes having a diameter of about 0.02 inches.

The cover sleeve 304 may be formed from an acrylic, polymer or polycarbonate or other translucent or clear material. In connection with a cover sleeve 304 that includes perforations 308 and is generally left in place about the exterior of the inner chamber 112 while collecting tissue, the sleeve 304 will generally be formed from a transparent material, to permit viewing of the interior of the inner chamber 112. Furthermore, the interior diameter of the cover sleeve 304 may be slightly smaller than the external diameter of the inner chamber 112, to provide a tight fit and may be split. In accordance with still other embodiments, the sleeve 304 may be adapted for insertion inside the inner chamber 112, in which case it should be formed from a thin material, for example a stiff walled tube having a wall thickness of about 0.04 inch. If holes or perforations 316 are provided, they may be about the same size as the holes or perforations 164 in its inner chamber 112.

In accordance with embodiments of the present invention, a tissue transplantation device 100 may be a disposable device that is not intended for reuse. In accordance with other embodiments of the present invention, a tissue transplantation device 100 may be capable of resterilization, to enable reuse. In accordance with still other embodiments of the present invention, components of a tissue transplantation device 100 may be reusable, while other components of that tissue transplantation device 100 may be disposable.

Although the foregoing contains particular ranges with respect to exemplary embodiments of the present invention, those dimensions are not intended to be limiting. Instead, they are examples of dimensions that have been found to be, or that are believed to be, useful in connection with particular implementations of embodiments of the present invention.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with the various modifications required by their particular application or use of the invention. It is intended that the appended claims be construed to include alternative embodiments to the extent permitted by the prior art.

What is claimed is:

1. A device for use in tissue transplantation, comprising:
   a substantially rigid outer chamber defining an interior volume including:
   an inlet fitting;
   at least a first substantially rigid inner chamber including:
   a substantially cylindrical body portion and a substantially cylindrical interior bore;
   a plurality of perforations in the body portion;
   an inlet at a distal end of the body portion, wherein the inlet is adapted for mating with the inlet fitting of the outer chamber; and
   an open proximal end;
   an integrated plug unit that includes an outer chamber seal having a first diameter that is received by an end of the outer chamber and an inner chamber seal having a second diameter that is received by an end of the inner chamber, an integrated plug unit fitting operable for interconnection to a vacuum device, and an opening, wherein the integrated plug unit fitting is in communication with the opening, the interior volume of the outer chamber, and an exterior of the inner chamber, and wherein the integrated plug unit fitting and the opening of the integrated plug unit are only in communication with an interior bore and the inlet of the inner chamber through the plurality of perforations in the body portion of the inner chamber.

2. The device of claim 1, wherein the device is capable of at least first and second modes of operation, and wherein in the first mode of operation the inner chamber is located within the interior volume of the outer chamber, and the integrated plug unit is received by the open proximal end of the inner chamber, and wherein in the second mode of operation the inner chamber is not located within the outer chamber, an inner chamber sleeve is placed over the perforations of the body portion of the inner chamber, the integrated plug unit is removed from the inner chamber, and a plunger is inserted into the interior bore of the inner chamber.

3. The device of claim 1, further comprising:
   a fluid reservoir in communication with the inlet of the at least a first inner chamber.

4. The device of claim 1, further comprising:
   a fluid reservoir; and
   a valve, wherein the fluid reservoir is in communication with the inlet of the at least a first inner chamber when the valve is in an open position.

5. The device of claim 1, further comprising a tissue conduit, wherein the tissue conduit comprises a cannula.

6. The device of claim 1, further comprising a tissue conduit, wherein the tissue conduit includes a cannula interconnected to the inlet by flexible tubing.

7. The device of claim 1, wherein the substantially rigid outer chamber further includes a seat for receiving the inlet of the first inner chamber.

8. The device of claim 1, wherein the inlet of the at least a first inner chamber comprises a luer lock.

9. The device of claim 2, wherein the inner chamber sleeve has a plurality of perforations, wherein in the first mode of operation the inner chamber sleeve is aligned such that at least most of the plurality of perforations in the inner chamber sleeve are aligned with one of the perforations of the plurality of perforations in the inner chamber, wherein the interior bore is in communication with the interior volume of the outer chamber through at least most of the plurality of perforations in the inner chamber sleeve, and wherein in the second mode of operation the position of the inner chamber sleeve is changed from the position of the inner chamber sleeve in the first mode such that the perforations of the inner chamber are not aligned with the perforations of the inner chamber sleeve.

10. The device of claim 9, wherein in the second mode of operation the inner chamber is removed from the interior volume of the outer chamber, and the inner chamber sleeve is aligned so that the all of the plurality of perforations in the body portion of the inner chamber are covered by solid portions of the inner chamber sleeve.

11. The device of claim 1, further comprising:
a plunger adapted for insertion within the substantially cylindrical bore of the inner chamber; and
an inner chamber sleeve adapted to cover the plurality of perforations in the body portion of the inner chamber, wherein communication between the interior bore and an exterior of the inner chamber through the plurality of perforations is blocked by the sleeve.

12. The device of claim 11, wherein the inner chamber is removed from the interior volume of the outer chamber, the integrated plug unit is removed from the open proximal end of the inner chamber body portion, the plunger is inserted in the cylindrical bore of the inner chamber, and the sleeve is in place to cover the plurality of perforations in the body portion of the inner chamber.

13. A device for use in tissue transplantation, comprising:
a tissue conduit;
a substantially rigid outer chamber defining an interior volume including:
an outlet fitting, wherein the interior volume may be placed in communication with a vacuum source;
an inlet fitting;
at least a first substantially rigid inner chamber including:
a substantially cylindrical body portion and a substantially cylindrical interior bore;
a plurality of perforations in the body portion;
an inlet at a distal end of the body portion, wherein the inlet is adapted for mating with the inlet fitting of the outer chamber;
an open proximal end;
a plug member adapted to be received by at least the open proximal end of the inner chamber;
a plunger adapted for insertion within the substantially cylindrical bore of the inner chamber;
an inner chamber sleeve adapted to cover the plurality of perforations in the body portion of the inner chamber, wherein communication between the interior bore and an exterior of the inner chamber through the plurality of perforations is blocked by the sleeve;
wherein the inner chamber is removed from the interior volume of the outer chamber, the plug member is removed from the open proximal end of the inner chamber body portion, the plunger is inserted in the cylindrical bore of the inner chamber, and the sleeve is in place to cover the plurality of perforations in the body portion of the inner chamber; and wherein the perforations do not extend along at least a first line along the substantially cylindrical body portion of the inner chamber, wherein the inner chamber sleeve is split, and wherein the split in the inner chamber is placed over said first line and the inner chamber sleeve covers substantially all of the cylindrical body portion of the inner chamber.

14. The device of claim 11, wherein the inner chamber sleeve is inserted inside the substantially cylindrical bore, and wherein the plunger is inserted within the inner chamber sleeve.

15. The device of claim 1, further comprising:
a plurality of the inner chambers, wherein in a first mode of operation at least more than one of the inner chambers is located within the interior volume of the outer chamber.

16. The device of claim 1, further comprising:
an absorption stick, wherein in a first mode of operation the absorption stick is located within the interior bore of the inner chamber.

17. The device of claim 1, wherein the integrated plug unit includes an interior bore, the device further comprising:
an inner syringe center tube having an open proximal end and a plurality of perforations held within the interior bore of the integrated plug unit, wherein the interior bore of the inner chamber is additionally in communication with the interior of the outer chamber through the plurality of perforations and the open proximal end of the inner syringe center tube when the device is in a first mode of operation.

18. The device of claim 1, further comprising a vacuum source interconnected to an outer chamber outlet fitting by a suction line.

19. The device of claim 1, wherein the outer chamber includes an open proximal end.

20. The device of claim 19, wherein the opening of the integrated plug unit
is located between the inner chamber seal and the outer chamber seal.

21. The device of claim 20, wherein the integrated plug unit further includes a perforated central suction tube.

22. The device of claim 1, wherein the perforations each have a diameter of about 0.02 inches.

23. The device of claim 1, wherein the inlet of the at least a first inner chamber has an inner diameter of at least 0.07 inches.

24. A device, comprising:
a rigid outer chamber, including:
an inlet at a distal end; and
an open proximal end;
a rigid inner chamber, including:
an inlet at a distal end;
a body portion, including a plurality of perforations;
an open proximal end;
an integrated plug unit, including:
an inner chamber seal operable to seal the open proximal end of the inner chamber;
an outer chamber seal operable to seal the open proximal end of the outer chamber;
an opening;
a fitting in communication with the opening and adapted for interconnection to a vacuum line, wherein in a first mode of operation the inner chamber is contained within the outer chamber, the inlet of the inner chamber is received by the inlet of the outer chamber, the inner chamber seal of the integrated plug unit is received by the open proximal end of the inner chamber, the outer chamber seal of the integrated plug unit is received by the open proximal end of the outer chamber, and the inlet of the rigid inner chamber is in communication with the fitting of the integrated plug unit through the perforations in the body portion of the inner chamber and the opening in the integrated plug unit.

25. The device of claim 24, further comprising:

a sleeve;

a plunger, wherein in a second mode of operation the integrated plug unit is removed from the outer chamber and the inner chamber, the inner chamber is removed from the outer chamber, the perforations in the body of the inner chamber are covered by the sleeve, and the plunger is placed in the open proximal end of the inner chamber.

26. The device of claim 24, further comprising:

a sleeve, wherein the sleeve has an inner diameter that receives the body portion of the inner chamber, covering the perforations;

a plunger, wherein the plunger is received by an interior bore of the inner chamber.

* * * * *